United States Patent [19]

Bergy et al.

[11] 4,271,266

[45] Jun. 2, 1981

[54] PROCESS FOR PREPARING LINCOMYCIN

[75] Inventors: Malcolm E. Bergy; John H. Coats; Vedpal S. Malik, all of Kalamazoo, Mich.

[73] Assignee: The Upjohn Manufacturing Company, Wilmington, Del.

[21] Appl. No.: 477,766

[22] Filed: Jun. 10, 1974

[51] Int. Cl.³ .............................................. C12P 19/64
[52] U.S. Cl. ...................................... 435/73; 435/886
[58] Field of Search ................ 195/80 R; 435/73, 886

[56] References Cited

U.S. PATENT DOCUMENTS 3,833,475  9/1974  Reusser et al. .................... 195/80 R Primary Examiner—Robert J. Warden
Attorney, Agent, or Firm—Roman Saliwanchik

[57] ABSTRACT

Microbiological process for preparing the antibiotic lincomycin at temperatures ranging from 18° C. to 45° C. using the newly discovered microorganism *Streptomyces vellosus*. The subject process advantageously results in the preparation of lincomycin without the concomitant production of lincomycin B (4'-depropyl-4'-ethyllincomycin). The absence of lincomycin B production results in increased lincomycin recovery efficiency.

4 Claims, No Drawings

PROCESS FOR PREPARING LINCOMYCIN

BACKGROUND OF THE INVENTION

The antibiotic lincomycin, formerly known as lincolnensin, can be produced by the microorganism *S. lincolnensis* var. *lincolnensis*, NRRL 2936, as disclosed in U.S. Pat. No. 3,086,912. The incubation temperature range disclosed in said patent for the production of lincomycin is 18° to 40° C., and preferably 26° to 30° C. Also produced during the lincomycin fermentation is the compound known as lincomycin B. Though lincomycin and lincomycin B have activity against essentially the same spectrum of microorganisms, it is known that lincomycin B is significantly less active against said microorganisms than is lincomycin. Accordingly, lincomycin is the preferred antibiotic of the two.

In conducting the above fermentation, it is necessary to use a large amount of cooling water in most fermentation equipment to maintain the desired fermentation temperature. Further, the maintenance of a temperature within the range of 18° C. to 40° C., though essential for antibiotic production as disclosed above, is conducive to the development and proliferation of contaminating microorganisms in the fermentation vessel.

BRIEF SUMMARY OF THE INVENTION

The subject invention concerns the fermentation preparation of lincomycin by the novel microorganism *Streptomyces vellosus* var. vellosus, NRRL 8037, at a temperature range of 18° to 45° C. It has been found, unexpectedly, that the titer of lincomycin produced at 45° C. is comparable to that which is produced at 28° C. The production of lincomycin at 28° C. and 45° C. for the microorganism of the subject invention is shown in the following table. The zone sizes of inhibition are given in millimeters. The test is a standard microbiological disc plate assay using 13 mm. paper discs.

| Organism | 28° C. | 45° C. |
|---|---|---|
| *Bacillus subtilis* | 21 | 18 |
| *Staphylococcus aureus* | 22 | 24 |
| *Sarcina lutea* | 31 | 29 |
| *Klebsiella pneumoniae* | 0 | 0 |
| *Escherichia coli* | 0 | 0 |
| *Salmonella schottmuelleri* | 0 | 0 |
| *Mycobacterium avium* | 22 | 25 |
| *Penicillium oxalicum* | 0 | 0 |

The results shown in the above table are unexpected since our tests have shown that *S. lincolnensis* var. *lincolnensis*, NRRL 2936, does not produce lincomycin when incubated at a temperature of about 45° C.

A distinct advantage in using this microorganism to prepare lincomycin is the need for less fermentor cooling capacity. The need for less cooling capacity is especially significant in high temperature climates and in areas having limited water supplies since water is the generally used means for cooling and maintaining fermentation temperatures. A further distinct advantage in the process of the subject invention is that lincomycin is produced without the concomitant production of lincomycin B.

DETAILED DESCRIPTION OF THE INVENTION

THE MICROORGANISM

The novel actinomycete used according to this invention for the production of lincomycin is *Streptomyces vellosus*. One of its strain characteristics is the production of lincomycin without the concomitant production of lincomycin B. Another of its strain characteristics is the production of comparable titers of lincomycin at a temperature of 28° C. and 45° C. A subculture of this living organism can be obtained upon request from the permanent collection of the Northern Regional Research Laboratories, Agricultural Research Services, U.S. Department of Agriculture, Peoria, Illinois, U.S.A. Its accession number in this repository is NRRL 8037.

The microorganism of this invention was studied and characterized by Alma Dietz of the Upjohn Research Laboratory.

A thermoduric Streptomyces species isolated from Arizona soil produces the antibiotic lincomycin. The culture is readily differentiated from other lincomycin-producers as may be noted in Table 4. The thermoduric property, the microscopic characteristics of long, straight spore chains coiled at the tip, spores with long spines and hairs, and the distinctive antibiotic-producing capability of *Streptomyces vellosus* are not reported for any of the Streptomyces species with blue-gray spore color mass cited in the significant Streptomyces taxonomy publications of Hütter [Hütter, R. 1967. Systematik der Streptomyceten unter besondere Berücksichtigung der von ihnen gebildeten Antibiotica. S. Karger, Basel], Krassilnikov [Krassilnikov, N. A. et al. 1966. Biology of Antibiotic-Producing Actinomycetes. Akademiya Nauk SSSR. Edited by Ya. I. Rautenstein. Published for the U.S. Department of Agriculture and the National Science Foundation, Washington, D.C. by the Israel Program for Scientific Translations], Kutzner [Kutzner, H. J. 1956. Beitrag zur Systematik und Ökologie der Gattung Streptomyces Waksm. et Henrici. Diss. Landw. Hochst. Hohenhein], Pridham, et al [Pridham, T. G., C. W. Hesseltine, and R. G. Benedict. 1958. A guide for the classification of streptomycetes according to selected groups. Placement of strains in morphological section. Applied Microbiol. 6:52–79], Shirling and Gottlieb [Shirling, E. B., and D. Gottlieb. 1968. Cooperative description of type cultures of Streptomyces. II. Species descriptions from first study. Int. J. Of Syst. Bacteriol. 18:69–189; Shirling, E. B. and D. Gottlieb. 1968. Cooperative description of type cultures of Streptomyces. III. Additional species descriptions from first and second studies. Int. J. of Syst. Bacteriol. 18:279–392; Shirling, E. B. and D. Gottlieb. 1969. Cooperative description of type cultures of Streptomyces. IV. Species descriptions from the second, third and fourth studies. Int. J. Of Syst. Bacteriol. 19:391–513; and Shirling, E. B. and D. Gottlieb. 1972. Cooperative description of type strains of Streptomyces V. Additional descriptions. Int. J. of Syst. Bacteriol. 22:265–394], Trejo [Trejo, W. H. and R. E. Bennett. 1963. Streptomyces species comprising the blue-spore series. J. Bacteriol. 85:676–690], or Waksman [Waksman, S. A. 1961. The actinomycetes, vol. 2, Classification, identification, and descriptions of genera and species. The Williams & Wilkins Co., Baltimore]. Therefore, it is proposed that this isolate be designated *Streptomyces vellosus* Dietz, sp.n. and that this type species be designated the type variety *Streptomyces vellosus* var. *vellosus*. The species and variety designations are made in accordance with the Rules set forth in the International Code of Nomenclature of Bacteria [International Code of Nomenclature of Bacteria. 1966. Edited by the Editorial Board of the Judicial Commission of the International Committee on Nomenclature of Bacteria. Int. J. Syst. Bacteriol. 16:459–490].

*Streptomyces vellosus* Dietz, sp. n.

Color characteristics. Aerial growth blue-gray to gray. Melanin-positive. Color on Ektachrome [Dietz, A. 1954. Ektachrome transparencies as aids in actinomycete classification. Ann. N.Y. Acad. Sci. 60:152–154] is given in Table 1. Reference color characteristics are given in Table 2. *Streptomyces vellosus* may be placed in the Blue (B) and White (W) color series of Tresner and Backus [Tresner, H. D., and E. J. Backus. 1962. System of color wheels for Streptomycete taxonomy. Applied Microbiol. 11:335–338].

Microscopic characteristics. Spore chains long, straight with a tight to open coil at the tip. Spore chains spiral (S) as defined by Pridham et al. [Pridham, T. G., C. W. Hesseltine, and R. G. Benedict. 1958. A guide for the classification of streptomycetes according to selected groups. Placement of strains in morphological sections. Applied Microbiol. 6:52–79]. Spores large, mostly oval. Spore surface adorned with long spines and hairs. Spore surface hairy as defined by Dietz and Mathews [Dietz, A. and J. Mathews. 1971. Classification of streptomyces spore surfaces into five groups. Appl. Microbiol. 21:527–533].

Cultural and biochemical characteristics. See Table 3. Carbon utilization. The growth of *S. vellosus* on carbon compounds was determined using the snythetic media of Pridham and Gottlieb [Pridham, T. G., and D. Gottlieb, 1948. The utilization of carbon compounds by some Actinomycetales as an aid for species determination. J. Bacteriol. 56:107–114] and of Shirling and Gottlieb [Shirling, E. B., and D. Gottlieb. 1966. Methods for characterization of Streptomyces species. Int. J. of Syst. Bacteriol, 16:313–340]. In the former, the culture showed trace growth on the control (basal medium without a carbon compound), dulcitol, D-sorbitol, sodium oxalate, and sodium tartrate, moderate growth on sodium acetate, sodium citrate, and sodium succinate; good growth on D-xylose, L-arabinose, rhamnose, D-fructose, D-galactose, D-glucose, D-mannose, maltose, sucrose, lactose, cellobiose, raffinose, dextrin, inulin, soluble starch, glycerol, D-mannitol, and inositol. The culture did not grow on salicin, phenol, cresol, sodium fomate or sodium salicylate. In the medium of Shirling and Gottlieb the culture grew slightly on the negative control (basal medium without a carbon compound) as well on the positive control (basal medium with D-glucose). Growth was equal to or better than on the basal medium plus glucose on D-xylose, inositol, D-mannitol, rhamnose and raffinose. Growth was significantly better than on the negative control but less than on the D-glucose control on L-arabinose, sucrose, and D-fructose. Growth on cellulose was doubtful.

Temperature. *S. vellusus* is a thermoduric actinomycete. It grows well at temperatures of 18–55 C. Optimum growth occurs at 28–37 C. in 10–14 days; at 45° C. in 48 hours.

Antibiotic-producing properties. *S. vellosus* produces the antibiotic lincomycin.

Source. Soil from Arizona.

Type culture. *Streptomyces vellosus* Dietz. sp.n. NRRL 8037.

Type variety. *Streptomyces vellosus* var. *vellosus* NRRL 8037.

TABLE 1

| Appearance of *Streptomyces vellosus* on Ektachrome* | | |
|---|---|---|
| Agar Media | Surface | Reverse |
| Bennett's | Gray | Tan-brown |
| Czapek's sucrose | Trace gray | Yellow-tan |
| Maltose tryptone | — | Brown |
| Peptone-iron | — | Brown |
| 0.1% Tyrosine | Trace blue-gray | Brown |
| Casein-starch | Blue-gray | Tan-brown |

*Dietz, A. 1954. Ektachrome transparencies as aids in actinomycete classification. Ann. N.Y. Acad. Sci. 60:152–154.

TABLE 2

| | Reference Color Characteristics of *Streptomyces vellosus* | | |
|---|---|---|---|
| Agar medium | Determination | Color Harmony Manual 3rd ed., 1948* | NBS Circular 553, 1955** |
| Bennett's | S | 15ba (g) to 5ba blue tint to shell pink | 184m very pale blue<br>189gm bluish white<br>9m pinkish white |
| | R | 3gc light tan | 76gm light yellowish brown |
| | P | 3ie camel, maple sugar, Tan | 76m light yellowish brown<br>77g moderate yellowish brown |
| Czapek's sucrose | S | 3cb sand | — |
| | R | 3ec bisque, light beige | 79gm light grayish yellowish brown<br>90 grayish yellow |
| | P | — | |
| Maltose-tryptone | S | 5ba shell pink | 9 pinkish white |
| | R | 31g adobe brown, cinnamon brown, light brown | 77gm moderate yellowish brown |
| | P | 3ie camel, maple sugar, tan | 76m light yellowish brown<br>77g moderate yellowish brown |
| Hickey-Tresner | S | 15ba to 3cb blue tint to sand | 184m very pale blue<br>189gm bluish white |
| | R | 31g adobe brown, cinnamon brown, light brown | 77m moderate yellowish brown |
| | P | 31e cinnamon, yellow maple | 74g strong yellowish brown<br>76m light yellowish brown |
| Yeast extract-malt extract (ISP-2) | S | 15ba to 2ba blue tint to pearl, shell tint | 184m very pale blue<br>189gm bluish white<br>92gm yellowish white |
| | R | 3b | 74g strong yellowish brown |

TABLE 2-continued

Reference Color Characteristics of *Streptomyces vellosus*

| Agar medium | Determination | Color Harmony Manual 3rd ed., 1948* | NBS Circular 553, 1955** |
|---|---|---|---|
| | P | 31e | 76m light yellowish brown<br>74g strong yellowish brown<br>76m light yellowish brown |
| Oatmeal (ISP-3) | S | 15cb cloud blue<br>190g light bluish gray | 184m very pale blue |
| | R | 2gc bamboo, chamois | 90 gm grayish yellow |
| | P | — | — |
| Inorganic-salts starch (ISP-4) | S | 19dc aqua gray | 149g pale green<br>190m light bluish gray |
| | R | 2fb bamboo, buff, straw, wheat | 87g moderate yellow<br>89m pale yellow |
| | P | — | — |
| Glycerol-asparagine (ISP-5) | S | 15ba blue tint | 184m very pale blue<br>189gm bluish white |
| | R | 2fb bamboo, buff, straw, wheat | 87g moderate yellow<br>89m pale yellow |
| | P | — | — |

S = Surface
(g) = all from glossy surface of color chip
R = Reverse
g = glossy surface of color chip
P = pigment
m = matte surface of color chip
gm = glossy or matte surface of color chip
*Jacobson, E., W. C. Granville, and C. E. Foss. 1948. Color harmony manual, 3rd ed. container Corporation of America, Chicago, Illinois.
**Kelly, K. L., and D. B. Judd. 1955. The ISCC-NBS method of designating colors and a dictionary of color names. U.S. Dept. Comm. Circ. 553.

TABLE 3

Cultural and Biochemical Characteristics of *Streptomyces vellosus*

| Medium | Surface (aerial growth) | Reverse | Other Characteristics |
|---|---|---|---|
| Agar media | | | |
| Peptone-iron | None at 28 C.<br>Gray at 45 C. | Brown | Brown pigment<br>Melanin-positive |
| Calcium-malate | Trace white | Colorless | No pigment<br>Malate not solubilized |
| Glucose-asparagine | Pale pink-white | Cream at 28 C.<br>Olive at 45 C. | Yellow pigment at 28 C.<br>No pigment at 45 C. |
| Skim milk | Trace gray at 28 C.<br>None at 45 C. | Tan brown | Tan brown pigment<br>Casein not solubilized |
| Tyrosine | Trace gray at 28 C.<br>Fair gray at 45 C. | Brown at 28 C.<br>Tan at 45 C. | Brown pigment at 28 C.<br>Tan pigment at 45 C.<br>Tyrosine not solubilized at 28 C.<br>Tyrosine solubilized under growth at 45 C. |
| Xanthine | None at 28 C.<br>Pink white at 45 C. | Yellow | Yellow pigment<br>Xanthine not solubilized |
| Nutrient starch | None at 28 C.<br>Pink-white at 45 C. | Yellow tan at 28 C.<br>Yellow at 45 C. | Yellow tan pigment at 28 C.<br>Yellow pigment at 45 C.<br>Starch not hydrolyzed |
| Yeast extract-malt extract | Pink white (best at 45 C.) | Red tan at 28 C.<br>Tan at 45 C. | Red tan pigment at 28 C.<br>Tan pigment at 45 C. |
| Bennett's | Pale cottony blue-white | Tan | Tan pigment |
| Czapek's sucrose | Pale cream pink | Yellow | Yellow pigment |
| Maltose-tryptone | Pale cottony blue-white | Brown | Brown pigment |
| Hickey-Tresner | Pale cottony blue-white | Orange-tan | Pale tan pigment |
| Peptone-yeast extract-iron (ISP-6) | None | Brown | Brown pigment<br>Melanin-positive |
| Tyrosine (ISP-7) | Pink-white | Brown | Brown Pigment<br>Melanin-positive |
| Gelatin Media | | | |
| Plain | — | — | Brown pigment at surface<br>Olive pigment top half<br>No liquefaction |
| Nutrient | — | — | Brown pigment at surface<br>Tan pigment throughout<br>No liquefaction - 2 tubes<br>Trace liquefaction - 2 tubes |
| Broth media | | | |
| Synthetic nitrate | — | — | Colorless vegetative growth throughout broth and at |

TABLE 3-continued

| Medium | Cultural and Biochemical Characteristics of *Streptomyces vellosus* | | |
|---|---|---|---|
| | Surface (aerial growth) | Reverse | Other Characteristics |
| Nutrient nitrate | — | — | base<br>No pigment<br>Nitrate not reduced to nitrite<br>Colorless compact bottom growth<br>Yellow pigment<br>Nitrate not reduced to nitrite |
| Litmus milk | White-gray aerial growth on surface ring | — | Brown pigment<br>Litmus reduced<br>pH 6.8 |

TABLE 4

Comparison of *Streptomyces vellosus* with other lincomycin-producers

| | S. vellosus<br>NRRL 8037 | S. lincolnensis<br>NRRL 2936 | S. espinosus<br>NRRL 3890 |
|---|---|---|---|
| Aerial mycelium | Blue gray to gray | Cream to pink to gray | Gray green |
| Melanin | Positive | Positive | Negative |
| Spore chains | Spiral (S)-very long and coiled at tip | Long flexuous (RF) | Short, straight to flexuous to open spiral (RF,RA)-short |
| Spores | Spherical | Rectangular | Spherical |
| Spore surface | Long spines and hairs | Smooth with surface detail | Thorny to spiny-transition to hairy on some spines |
| Calcium malate agar | Malate not solubilized | Malate not solubilized | Malate not solubilized |
| Skim milk agar | Casein not solubilized | Casein not solubilized | Casein solubilized |
| Tyrosine | Not solubilized | Solubilized | Solubilized |
| Xanthine | Not solubilized | Solubilized around growth | Not solubilized |
| Nutrient starch | Starch not hydrolyzed | Starch hydrolyzed | Starch hydrolyzed |

| | S. pseudogriseolus<br>chemovar linmyceticus<br>NRRL 3985 | S. variabilis<br>chemovar liniabilis<br>NRRL 5618 |
|---|---|---|
| Aerial mycelium | Gray to white to red | Gray to white |
| Melanin | Negative | Negative |
| Spore chains | Short to moderately long straight (RF) to open spiral (RA) to spiral (S) | Short to moderately long flexuous (RF) to open spiral (RA) |
| Spores | Oval to oblong | Oval to oblong |
| Spores surface | Sparsely spiny to smooth | Smooth to poorly warty to spiny |
| Calcium malate agar | Malate not solubilized | Malate solubilized |
| Skim milk agar | Casein solubilized under growth | Casein solubilized |
| Tyrosine | Solubilized | Solubilized |
| Xanthine | Solubilized | Solubilized |
| Nutrient starch | Starch hydrolyzed | Starch hydrolyzed around growth |

Lincomycin is produced by the novel microorganism of the subject invention when said microorganism is grown in an aqueous nutrient medium under submerged aerobic conditions. It is to be understood also that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include corn steep liquor, yeast, autolyzed brewer's yeast with milk solids, soybean meal, cottonseed meal, cornmeal, milk solids, pancreatic digest of casein, distillers' solids, animal peptone liquors, fishmeal, meat and bone scraps, and the like. Combinations of these carbon and nitrogen sources can be used advantageously. Trace metals, for example, zinc, magnesium, manganese, cobalt, iron, and the like, usually need not be added to the fermentation media since tap water and unpurified ingredients are used as media components.

Production of lincomycin by the process of the subject invention can be effected at a temperature of about 18° to about 45° C., and preferably at a temperature of about 20° C. to about 45° C. Ordinarily, optimum production of lincomycin is obtained in about two to ten days. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of lincomycin and the attendant inefficient utilization of the equipment. Accordingly, it is desirable to produce a vegetative inoculum in a nutrient broth culture by inoculating this broth culture with an aliquot from a soil or a slant culture. When a young, active vegetative inoculum has thus been secured, it is transferred aseptically to large vessels or tanks. The medium in which the vegetative inoculum is produced can be the same as, or different from, that utilized for the production of lincomycin, as long as it is such that a good growth of the microorganism is obtained.

The lincomycin produced by the subject process can be recovered by the procedure disclosed in U.S. Pat. No. 3,086,912.

In preferred recovery process, lincomycin is recovered from its culture medium by separation of the mycelia and undissolved solids by conventional means, such as by filtration and centrifugation. Lincomycin is then recovered from the filtered or centrifuged broth by passing said broth over a resin which comprises a non-ionic macro porous copolymer of styrene crosslinked with divinylbenzene. Resins of this type are disclosed in U.S. Pat. No. 3,515,717. Exemplary of this type of resin in Amberlite XAD-2. Lincomycin is eluted from the resin with a solvent system consisting of methanol water (95:5 v/v). Bioactive eluate fractions are determined by a standard microbiological disc plate assay using the microorganism *Sarcina lutea*. Biologically active fractions are combined, concentrated to an equeous solution which is then freeze dried. The freeze dried material is then triturated with methylene chloride. The methylene chloride extract is concentrated to dryness and the residue triturated with acetone. The filtrate is mixed with ether to give a precipitate which is separated. The remaining filtrate is mixed with methanolic hydrogen chloride (1 N) to precipitate colorless lincomycin hydrochloride. This precipitate is isolated by filtration and crystallation from water-acetone to give crystalline lincomycin hydrochloride.

The process of the subject invention is not limited to the particular microorganism fully described by the cultural characteristics disclosed herein. It is intended that this invention also include other lincomycin-producing strains or mutants of the said microorganism which can be produced by procedures well known in the art, for example, by subjecting the novel microoganism to x-ray or ultraviolet radiation, nitrogen mustard, phage exposure, and the like.

Hereinafter is described a non-limiting example of the process of the present invention. All percentages are by weight and all solvent portion mixtures are by volume unless otherwise noted.

EXAMPLE 1

Part A. FERMENTATION AT 28° C.

A soil slant of *Streptomyces vellosus*, NRRL 8037, is used to inoculate a series of 500-ml. Erlenmeyer flasks containing 100-ml. of sterile seed medium consisting of the following ingredients:
Glucose monohydrate: 25 g./liter
Pharmamedia*: 25 g./liter
Tap water q.s.: Balance
Presterilization pH=7.2
*Pharmamedia is an industrial grade of cottonseed flour produced by Traders Oil Mill Company, Fort Worth, Texas.

The flasks are grown for 3 days at 28° C., on a rotary shaker.

Seed inoculum, described above, is used to inoculate a series of 500-ml. Erlenmeyer fermentation flasks containing 100-ml. of sterile medium consisting of the following ingredients:
Glucose monohydrate: 15 g./liter
Wilson's Peptone Liquor No. 159*: 15 g./liter
Difco Yeast Extract**: 2.5 g./liter
Tap water q.s.: Balance
Presterillization pH=6.0
*Wilson's Peptone Liquor No. 159 is a preparation of hydrolyzed proteins of animal origin.
**Supplied by Difco Laboratories, Detroit, Michigan.

The flasks are inoculated with 5 ml. of seed inoculum per 100 l ml. of fermentation medium. The flasks are then incubated at 28° C. on a rotary shaker operating at 250 rpm with a 6 cm. stroke. The flasks are harvested after 96 hours of fermentation.

Part B. FERMENTATION AT 45° C.

Seed inoculum, as described above in Part A, is used to inoculate a series of 500-ml. Erlenmeyer fermentation flasks containing 100 ml. of sterile medium consisting of the following ingredients:
Glycerol: 30 g./liter
NZ-amine B*: 20 g./liter
Difco Yeast Extract: 2 g./liter
Sodium chloride: 3 g./liter
Tap water q.s.: Balance
Presterilization pH=7.2
A bulk peptone in powder form obtained by the pancreatic digestion of casein.

The flasks are inoculated with 5 ml. of seed inoculum per 100 ml. of fermentation medium. The flasks are then incubated at 45° C. on a rotary shaker operating at 250 rpm with a 6 cm. stroke. The flasks are harvested after 96 hours of fermentation.

Part C. RECOVERY

The lincomycin produced in the fermentations as disclosed in Parts A and B is recovered in pure form by first filtering the fermentation beers using diatomaceous earth as filter aid. The filter cake is washed with water and the wash is combined with the clear filtrate. The clear filtratewash is then passed over a column containing Amberlite XAD-2 resin packed in water. The lincomycin is eluted from the resin with methanol-water (95:5 v/v). Fractions are collected and analyzed by thin layer chromatography on silica gel G using the solvent system consisting of methyl ethyl ketone-acetone-water (186:52:20 v/v). Active fractions are combined and concentrated to an aqueous and freeze dried. The dry material is then triturated with methylene chloride. The methylene chloride extract is concentrated to dryness. The resulting residue is triturated with acetone. Insoluble material is removed by filtration and the remaining filtrate is mixed with ether. Again, precipitated material is removed by filtration and the remaining filtrate is mixed with methanolic hydrogen chloride (1 N). The resulting precipitated colorless lincomycin hydrochloride is isolated by filtration. This material is converted to the crystalline form by crystallzation from water-acetone.

The amount of lincomycin B in a normal fermentation of *Streptomyces lincolnensis* var. *lincolnensis* will vary with the media composition, incubation time and temperature, aeration, etc. Under normal operating conditions amounts of lincomycin B in such a fermentation will range from 5 to 10% of the total lincomycin present. The lincomycin B is removed by repeated recrystallization of the lincomycin product in suitable solvents, for example, water-acetone mixtures, or water-lower alcohol mixtures. Since the process of the subject invention does not produce lincomycin B, these crystallizations are unnecessary.

We claim:

1. A novel process for preparing the antibiotic lincomycin which comprises cultivating *Streptomyces vellosus*, having the identifying characteristics of NRRL 8037, and lincomycin-producing mutants thereof, in an aqueous nutrient medium under aerobic conditions until substantial antibiotic activity is imparted to said medium by the production of lincomycin.

2. A process, according to claim 1, wherein the cultivation is conducted at a temperature range of about 18° C. to about 45° C.

3. A process, according to claim 1, wherein said aqueous nutrient medum contains a source of assimilable carbohydrate and assimilable nitrogen.

4. A process. according to claim 1, wherein said lincomycin is isolated from the fermentation broth.

* * * * *